United States Patent
Masters et al.

(10) Patent No.: US 7,601,338 B2
(45) Date of Patent: Oct. 13, 2009

(54) ANTIPLAQUE ORAL COMPOSITION CONTAINING ENZYMES AND CYCLODEXTRINS

(75) Inventors: James G. Masters, Ringoes, NJ (US); Richard Payne, Brielle, NJ (US); Lori H. Szeles, Howell, NJ (US); Xiaoyan Liu, Highland Park, NJ (US); Malcolm Williams, Piscataway, NJ (US)

(73) Assignee: Colgate-Palmolive Co., New York, NY (US)

( * ) Notice: Subject to any disclaimer, the term of this patent is extended or adjusted under 35 U.S.C. 154(b) by 392 days.

(21) Appl. No.: 11/152,803

(22) Filed: Jun. 14, 2005

(65) Prior Publication Data

US 2006/0008425 A1    Jan. 12, 2006

Related U.S. Application Data

(63) Continuation of application No. 10/205,119, filed on Jul. 25, 2002, now abandoned.

(51) Int. Cl.
*A61Q 11/00* (2006.01)
*A61K 8/60* (2006.01)
*A61K 8/66* (2006.01)

(52) U.S. Cl. .......................... 424/50; 514/58
(58) Field of Classification Search .................. 424/50; 514/58

See application file for complete search history.

(56) References Cited

U.S. PATENT DOCUMENTS

| 5,524,906 A | 6/1996 | Rackov et al. |
| 2002/0028251 A1 | 3/2002 | Okay |

FOREIGN PATENT DOCUMENTS

| CA | 2386273 A1 | 2/2002 |
| DE | 100 59 105 A1 | 6/2002 |
| EP | 1 284 286 A1 | 2/2003 |
| JP | 2005205338 A2 | 8/2005 |
| WO | WO01/26617 | 4/2001 |
| WO | WO02/41920 A1 * | 5/2002 |
| WO | WO 0241920 A1 | 5/2002 |

OTHER PUBLICATIONS

Derwent Publications Ltd. XP002259481 & JP 05 205668A (Daiichi Kogyo Seiyaku Co. Ltd) Abstract May 11, 1977.
Patent Abstracts of Japan vol. 012, No. 410; Oct. 28, 1988 & JP 63 150217 (Kiyuushin Seiyaku KK), Jun. 22, 1988.
Patent Abstracts of Japan vol. 015, No. 500; Dec. 18, 1991 & JP 03 220117A (Morishita Jintan KK) Sep. 27, 1991.
M. Singh et al. "Biotecnological Applications of Cyclodextrins" Biotechnology Advances, vol. 20, No. 5-6; Dec. 2002, pp. 341-359.

* cited by examiner

*Primary Examiner*—Herbert J. Lilling
(74) *Attorney, Agent, or Firm*—Donald L. Traut

(57) ABSTRACT

An antiplaque oral care composition having enhanced oral hygiene and organoleptic properties is provided. The composition contains an enzyme and a cyclodextrin. Papain and other proteolytic enzymes may be preferred. The resulting composition has more favorable organoleptic properties than a comparative composition containing only the enzyme.

15 Claims, No Drawings

ANTIPLAQUE ORAL COMPOSITION CONTAINING ENZYMES AND CYCLODEXTRINS

CROSS REFERENCE TO RELATED APPLICATION

This application is a continuation of U.S. Ser. No. 10/205,119, filed Jul. 25, 2002, now abandoned the contents of which are incorporated herein by reference.

BACKGROUND OF THE INVENTION

Oral compositions such as toothpastes, gels and mouth washes are designed to loosen and remove plaque in conjunction with a regular toothbrushing regimen. Dental plaque is present to some degree, in the form of a film, on virtually all dental surfaces. It is a byproduct of microbial growth, and comprises a dense microbial layer consisting of a mass of microorganisms embedded in a polysaccharide matrix. Plaque itself adheres firmly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The danger associated with the formation of plaque on the teeth lies in the tendency of plaque to build up and eventually produce gingivitis, periodontitis and other types of periodontal disease, as well as dental caries and dental calculus.

It is known to the art to incorporate antimicrobial agents in oral compositions wherein these agents destroy or inhibit oral bacteria. Other agents are also incorporated in the oral composition to enhance the efficacy of the antimicrobial agents. For example, it is known to incorporate enzymes in oral compositions which disrupt or interfere with plaque formation and bacterial adhesion to tooth surfaces. Examples of such enzymes include glucose oxidase, galactose oxidase, lactose peroxidase, lactoferrin, lysozyme, proteolytic enzymes, pancreatic enzymes, bacterial enzymes (such as those obtained from *Bacillus subtilis*) lipolytic enzymes, dextranases (such as those from *Penicillin funiculosium*), and mixtures thereof.

Certain enzymes, as for example, proteolytic enzymes, such as papain, that enhance antibacterial efficacy at the levels wherein enhancement is observed, have been found to contribute to flavor (taste) problems whereby oral care products in which such enzymes are incorporated have limited acceptability for consumers. For example, the enzyme papain, which is naturally extracted from fruit, contains residual levels of impurities so that when papain is incorporated in an aqueous dentifrice or mouthwash, the impurities present adversely impact key consumer sensorial perceptions.

Attempts made to utilize flavoring ingredients to "mask" the taste problem and particularly the meaty notes introduced by these impurities, have met with limited success. There is therefore a need in the art for oral compositions imparting antiplaque and anti-malodor benefits in which enzymes are incorporated to provide a product of acceptable taste.

BRIEF SUMMARY OF THE INVENTION

In accordance with the present invention it has been unexpectedly determined that cyclodextrin compounds form insoluble complexes with the lipophylic, water insoluble impurities present in natural enzymes such as papain. The preferential entrapment and formation of an insoluble complex of the impurities with the cyclodextrin compound inhibits the partitioning of the impurity into the liquid phase of aqueous oral care compositions such as toothpastes and mouthwashes in which the enzyme is incorporated, whereby insolubilization of the impurities results in improved taste/organoleptic characteristics.

As will hereinafter be demonstrated, Gas Chromatographic analysis evidence significant reductions of several malodor creating impurities derived from enzymes such as papain present in aqueous oral care compositions and particularly hydrogen sulfide ($H_2S$) and dimethyl sulfide (DMS). These results were found to be consistent with blind flavor evaluations where the meaty, sulfur based notes normally encountered with enzymes such as papain were reduced by about 30%.

DETAILED DESCRIPTION OF THE INVENTION

As used herein, the term "cyclodextrin" includes any of the known cyclodextrins such as unsubstituted cyclodextrins containing from six to twelve glucose units, especially alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms; therefore, this surface is fairly hydrophobic. The unique shape and physical-chemical properties of the cavity enable the cyclodextrin molecules to absorb that is, form inclusion complexes with, organic molecules or parts of organic molecules including malodor compounds which fit into the cavity and become water insolubilized.

The derivatives of cyclodextrin consist mainly of molecules wherein some of the OH groups are converted to OR groups, wherein R is a methyl or an ethyl group. Cyclodextrin derivatives include those with short chain alkyl groups such as methylated cyclodextrins, and ethylated cyclodextrins, those with hydroxyalkyl substituted groups, such as hydroxypropyl cyclodextrins and/or hydroxyethyl cyclodextrins.

Beta-cyclodextrin is preferred for use in the practice of the present invention. The cyclodextrin is present in enzyme containing oral compositions at a concentration of about 0.1 to about 5% by weight of the composition.

The enzymes useful in the practice of the present invention include enzymes extracted from natural fruit products such as well-known protein substances within the class of proteases, which breakdown or hydrolyze proteins. The proteolytic enzymes are obtained from natural sources or by the action of microorganisms having a nitrogen source and a carbon source. Examples of proteolytic enzymes useful in the practice of the present invention include the naturally occurring enzymes papain (from papaya), bromelain (from pineapple), as well as serine proteases such as chymotrypsin. Additional enzymes include ficin and alcalase.

Papain obtained from the milky latex of the papaya tree is the proteolytic enzyme preferred for use in the practice of the present invention and is incorporated in the oral care composition of the present invention in an amount of about 0.1 to about 10% by weight and preferably about 0.2 to about 5% by weight, such papain having an activity of 150 to 900 units per milligram as determined by the Milk Clot Assay Test of the Biddle Sawyer Group (see J. Biol. Chem., vol. 121, pages 737-745).

Enzymes which may beneficially be used in combination with the proteolytic enzymes include carbohydrases such as glucoamylase, alpha-amylase, beta-amylase, dextranase and mutanase, tannase and lipases such as plant lipase, gastric lipase and pancreatic lipase.

Glucoamylase is a saccharifying glucoamylase which may be obtained from *Aspergillus niger*. This enzyme can hydrolyze both the alpha-D-1,6 glucosidic branch points and the alpha-1,4 glucosidic bonds of glucosyl oligosaccharides. The product of this invention comprises about 0.01 to 10% of the carbohydrases. The lipase enzyme is derived from a select strain of *Aspergillus niger*. The enzyme has maximum lipolytic activity at pH 5.0 to 7.0 when assayed with olive oil. The enzyme has 120,000 lipase units per gram. Among the carbohydrases useful in accordance with this invention are glucoamylase, alpha and beta-amylase, dextranase and mutanase.

Enzymes such as proteolytic enzymes are included in the oral composition of the present invention at a concentration of about 0.10 to about 5.0% by weight and preferably about 0.2 to about 2% by weight.

Orally-acceptable vehicles used to prepare dentifrice compositions include a water-phase, containing a humectant. The humectant is preferably glycerin, sorbitol, xylitol, and/or propylene glycol of molecular weight in the range of 200 to 1,000; but, other humectants and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 25 to 70% by weight of the oral composition. Water employed in the preparation of commercially suitable oral compositions should preferably be deionized and free of organic impurities. These amounts of water include the free water which is added plus that which is introduced with other materials such as with sorbitol.

In the preparation of dentifrice compositions abrasives which may be used in the practice of the present invention include silica abrasives such as precipitated silicas having a mean particle size of up to about 20 microns, such as ZEODENT® 115, marketed by J.M. Huber Chemicals Division, Havre de Grace, Md. 21078, or SYLODENT® 783 marketed by Davison Chemical Division of W.R. Grace & Company. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

Preferred abrasive materials useful in the practice of the preparation of dentifrice compositions in accordance with the present invention include silica gels and precipitated amorphous silica having an oil absorption value of less than 100 cc/100 g silica and preferably in the range of from about 45 cc/100 g to less than about 70 cc/100 g silica. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Oil absorption values are measured using the ASTM® Rub-Out Method D281. The low oil absorption silica abrasive is present in the oral are compositions of the present invention at a concentration of about 5 to about 40% by weight and preferably about 10 to about 30% by weight.

Low oil absorption silica abrasives particularly useful in the practice of the present invention are marketed under the trade designation SYLODENT® XWA by Davison Chemical Division of W.R. Grace & Co., Baltimore, Md. 21203. SYLODENT® 650 XWA, a silica hydrogel composed of particles of colloidal silica having a water content of 29% by weight averaging from about 7 to about 10 microns in diameter, and an oil absorption of less than 70 cc/100 g of silica is a preferred example of a low oil absorption silica abrasive useful in the practice of the present invention.

The dentifrice and mouthwash compositions of the present invention can contain a variety of optional ingredients. As described below, such optional ingredients can include, but are not limited to, thickening agents, surfactants, a source of fluoride ions, a synthetic anionic polycarboxylate, a flavoring agent, antibacterial agents, antitartar and coloring agents.

Thickeners used in the compositions of the present invention include natural and synthetic gums and colloids. Not all naturally occurring polymer thickeners (such as cellulose or carrageenans) are compatible with ingredients (specifically enzymes) of oral compositions when formulated in the presence of proteolytic enzymes. Thickeners compatible with enzymes such as proteolytic enzymes, include xanthan gum, polyglycols of varying molecular weights sold under the trade name POLYOX®, and polyethylene glycol. Compatible inorganic thickeners include amorphous silica compounds which function as thickening agents and include colloidal silicas compounds available under the trade designation CAB-O-SIL® manufactured by Cabot Corporation and distributed by Lenape Chemical, Bound Brook, N.J.; ZEODENT® 165 from J.M. Huber Chemicals Division, Havre de Grace, Md. 21078; and SYLODENT® 15, available from Davison Chemical Division of W.R. Grace Corporation, Baltimore, Md. 21203. Other inorganic thickeners include natural and synthetic clays, lithium magnesium silicate (LAPONITE®) and magnesium aluminum silicate (VEEGUM®).

The thickening agent is present in the dentifrice composition in amounts of about 0.1 to about 10% by weight, preferably about 0.5 to about 4.0% by weight.

Surfactants are used in the oral compositions of the present invention to achieve increased prophylactic action and render the compositions more cosmetically acceptable. The surfactant is preferably a detersive material which imparts to the composition detersive and foaming properties.

Anionic surfactants such as higher alkyl sulfates such as sodium lauryl sulfate are not compatible with enzymes. Anionic surfactants facilitate denaturing of the enzyme and loss in activity. As a result, it is important to the practice of the present invention to use a surfactant or combination of surfactants that are compatible with the enzymes present in the oral composition and provide the requisite foaming characteristics. Examples of enzyme compatible surfactants include nonanionic polyoxyethylene surfactants such as POLYAXAMER® 407, Steareth 30, Polysorbate 20, and PEG-40 castor oil and amphoteric surfactants such as cocamidopropyl betaine (tegobetaine) and cocamidopropyl betaine lauryl glucoside. Preferred surfactants include a concentration in the oral composition of between about 2 to about 10% by weight and preferably between about 3.5 to about 6.5% by weight.

The oral composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts. For example, preferred fluoride sources which are compatible with enzymes present in the composition are sodium fluoride, potassium fluoride, sodium fluorosilicate, sodium monfluorophosphate (MFP), ammonium fluorosilicate, as well as tin fluorides, such as stannous fluoride and stannous chloride. Sodium fluoride or MFP is preferred.

In addition to fluoride compounds, there may also be included in the oral compositions of the present inventions antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, polyphosphates such as sodium tripolyphosphate, sodium hexametaphosphate and cyclic phosphates such as sodium tripolyphosphate sodium trimetaphosphate. These antitartar agents are included in the dentifrice composition at a concentration of about 1 to about 5% by weight.

Another active agent useful in dentifrice compositions of the present invention are antibacterial agents, which can be from 0.2 to 1.0% by weight of the dentifrice composition. Such useful antibacterial agents include non-cationic antibacterial agents which are based on phenolic or bisphenolic compounds, such as halogenated diphenyl ethers such as Triclosan (2,4,4'-trichloro-2'-hydroxydiphenyl ether).

The oral compositions of the present invention may also contain ingredients which stabilize enzymes in a dentifrice environment. These stabilizers protect the enzyme from inactivation by chelating metal impurities present in the oral composition which have the propensity to denature the active site of the enzyme by protecting the enzyme from oxidation. For protease enzymes such as papain, sodium bisulfite and thiosulfites can be employed. Chelating agents include, ethylene diamine tetraacetic acid (EDTA) and sodium gluconate at concentrations between 0.01 and 1%, preferably between 0.1 and 0.5%. Agents stabilizing the enzyme against oxidation include sodium bisulfite, metal gallates, sodium stannate, 3,5,-di-tert-butyl-4-hydroxytoluene (BHT), Vitamin E ($\alpha$, $\beta$, $\gamma$.form s/Vitamin E acetate and ascorbic acid at concentrations between about 0.03 to about 1.5%, preferably between about 0.3 and about 0.75%. Additional chelating agents of mono- and di-charged cationic species include sodium tripolyphosphate and tetrasodium pyrophosphate.

Synthetic anionic polycarboxylates may also be used in the oral compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the trade name GANTREZ®, e.g., AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the oral composition. Generally, the anionic polycarboxylates is present within the oral composition from about 0.05% to about 4% by weight, preferably from about 0.5% to about 2.5% by weight.

The oral composition of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the oral composition at a concentration of about 0.1 to about 5% by weight and preferably about 0.5 to about 1.5% by weight.

Various other materials may be incorporated in the dentifrice and mouth wash compositions of this invention, including desensitizers, such as potassium nitrate; whitening agents, such as hydrogen peroxide, calcium peroxide and urea peroxide; preservatives; silicones; and chlorophyll compounds. These additives, when present, are incorporated in the oral compositions of the present invention in amounts which do not substantially adversely affect the properties and characteristics desired.

To prepare a dentifrice of the present invention, generally the humectants, such as glycerin, or sobitol, are dispersed in the water in a conventional mixer under agitation. Into the dispersion are added organic thickeners, such as xanthan gum; any anionic polycarboxylate; any salts, such as sodium fluoride anticaries agents; pH buffering agents such as sodium phosphate salts and reducing agents such as bisulfite salts, antitartar agents such as tetrasodium pyrophosphate, sodium tripolyphosphate and any sweeteners. The resultant mixture is agitated until a homogeneous gel phase is formed. Into the gel phase are added a pigment such as $TiO_2$, and any acid or base required to adjust the pH in the range of 6.4 to 7.3. These ingredients are mixed until a homogenous phase is obtained. Thereafter a dispersion in water of the enzyme and cyclodextrin compounds and a humectant such as polyethylene glycol is added and admixed with the homogeneous phase This mixture is then transferred to a high speed/vacuum mixer; wherein, the thickener, and surfactant ingredients are added to the mixture. Thereafter the abrasive is added. Any water insoluble antibacterial agent, such as Triclosan, is solubilized in the flavor oils to be included in the composition and the solution is added along with the surfactants to the mixture, which is then mixed at high speed for from 5 to 30 minutes, under vacuum of from about 20 to 50 mm of Hg, preferably about 30 mm Hg. The resultant product is in each case a homogeneous, semi-solid, extrudable paste or gel product.

In the aspect of the present invention wherein the oral composition is substantially liquid in character such as a mouthwash or rinse, the vehicle is typically a water alcohol mixture. Generally, the weight ratio of water to alcohol is in the range of from about 3:1 to 10:1 and preferably about 4:1 to 6:1. The alcohol is a non-toxic alcohol such as ethanol or isopropanol. A humectant such as glycerin, sorbitol or an alkylene glycol such as polyethylene glycol or propylene glycol may be present in an amount of about 10 to 30% by weight. Mouthwashes typically contain about 50 to 85% by weight water, about 0 to 20% by weight of a non-toxic alcohol and about 10 to 40% by weight of the humectant. Thickeners may be present at a concentration of about 1.0 to about 3.0% by weight, cyclodextrin at a concentration of about 0.1 to about 1.0% by weight and the enzyme present in the mouthwash at a concentration of about 0.02 to about 0.2% by weight and a flavor ingredient at a concentration of about 0.3 to about 1.0% by weight.

In the preparation of a mouthwash, the cyclodextrin/enzyme combination is dispersed in a mixture of ingredients, for example, alcohol, humectants, surfactants, and flavor are then added and mixed. The ingredients are then mixed under vacuum for about 15-30 minutes. The resulting mouthwash product is then packaged.

The following examples further describe and demonstrate preferred embodiments within the scope of the present invention. The examples are given solely for illustration, and are not to be construed as a limitation of this invention as many variations thereof are possible without departing from its spirit and scope.

EXAMPLE I

It has been determined that β-cyclodextrins can incorporate hydrophobic, non-polar species into its cavity to form insoluble complexes by treating a water/PEG-600/enzyme solution during the preparation of the oral composition wherein, impurities from the enzyme powder can be sequestered and removed from solution so that the highly insoluble nature of the complex disfavors partitioning of the hydrophobic impurity into the liquid phase of the composition significantly reducing its negative impact on taste and produce aroma.

To demonstrate the cyclodextrin complexing of impurities in the enzyme papain, 5 grams of the enzyme were dissolved in 95 milliliters of water. β-cyclodextrin (β-CD) was added at a weight ratio of 4/1 β-CD to enzyme. Analysis of the headspace of theses solutions revealed the presence of several impurities which were identified as carbonyl sulfide, acetone, methyl ethyl ketone, dimethyl sulfide, carbon disulfide and mesityl oxide all which negatively impact the organoleptic properties of the oral care composition.

Qualitative data for these the impurities (above) was obtained by Static Headspace Solid Phase Microextraction (HS-SPME) GC/MS analysis. Quantitation of sulfur volatiles was determined by Headspace Gas Chromatography—Flame Photometric Detection (HS-GC/FPD) analysis that focused on evaluating the intensity of two impurities, hydrogen sulfide and dimethyl sulfide. The HS-SPME GC/MS results are recorded in Table I. For purposes of comparison, the procedure of Example 1 was repeated except β-CD was not included in the test solution. The HS-SPME GC/MS results are also recorded in Table I below.

The results recorded in Table I demonstrate the significant reduction in malodor impurities derived from enzymes such as papain when a cyclodextrin compound is used in combination with the enzyme ingredient.

EXAMPLE II

A series of papain enzyme containing toothpaste compositions were prepared in which a β-CD/papain enzyme system was incorporated. The compositions which are illustrative of the present invention were designated Compositions B and D. β-CD was incorporated in Compositions B and D during the premixing of the papain enzyme with PEG-600 and water at a concentration of 2% by weight, or at a weight ratio of 4/1 β-CD/enzyme. Mixing time for the β-CD/enzyme slurry was 10 minutes. The β-CD/enzyme admixture was then incorporated into the dentifrice composition as the last step. The ingredients of Compositions B and D are listed in Table II below.

For purposes of comparison, the procedure of Example II was repeated except β-CD was not included in the compositions. These comparative toothpaste compositions, designated compositions A and C, and their ingredients, are also listed in Table II below.

TABLE II

| Ingredients | A | B | C | D |
| --- | --- | --- | --- | --- |
| Water | 16.0 | 16.0 | 16.0 | 16.0 |
| LAPONITE ® | 0.7 | 0.7 | 0.70 | 0.70 |
| Glycerin | 20.0 | 20.0 | 20.0 | 20.0 |
| Sodium tripolyphosphate | 3.0 | 3.0 | 3.0 | 3.0 |
| Trisodium pyrophosphate | 2.0 | 2.0 | 2.0 | 2.0 |
| Xanthan gum | 0.50 | 0.5 | 0.50 | 0.50 |
| Sodium phosphate monobasic | 0.03 | 0.03 | 0.03 | 0.03 |
| Sodium phosphate dibasic | 0.20 | 0.20 | 0.20 | 0.20 |
| Sodium bisulfite | 0.10 | 0.10 | 0.10 | 0.10 |
| Sodium saccharin | 0.40 | 0.40 | 0.40 | 0.40 |
| Na monofluorophosphate | 0.76 | 0.76 | 0.76 | 0.76 |
| Sorbitol | 21.235 | 19.235 | 19.735 | 17.735 |
| SYLODENT ® XWA650 | 20.0 | 20.0 | 20.0 | 20.0 |
| ZEODENT ® 115 | 5.0 | 5.0 | 5.0 | 5.0 |
| ZEODENT ® 165 | 2.0 | 2.0 | 2.0 | 2.0 |
| Titanium dioxide | 0.4 | 0.40 | 0.40 | 0.40 |
| Polysorbate 20 | 2.0 | 2.0 | 2.0 | 2.0 |
| Tegobetaine | 2.0 | 2.0 | 2.0 | 2.0 |
| PEG-600 | 3.0 | 3.0 | 3.0 | 3.0 |
| PEO-POLYOX ® | 0.075 | 0.075 | 0.075 | 0.075 |
| Papain | 0.50 | 0.50 | 0.50 | 0.50 |
| Glucoamylase | 0.10 | 0.10 | 0.10 | 0.10 |

TABLE I

Reduction of impurities found in the headspace of dentifrice compositions containing enzymes with and without β-CD as measured by HS-SPME GC/MS analysis.

| Retention Time | Impurity Compound | Peak Area* (β-CD absent) | Peak Area (β-CD/papain) | % Reduction |
| --- | --- | --- | --- | --- |
| 1.69 | Acetone | 475,825 | 11,842 | 97 |
| 1.97 | 2-butanone | 33,237 | 6,638 | 80 |
| 3.15 | Dimethyl sulfide | 76,891 | 22,367 | 71 |
| 3.84 | Mesityl oxide | 72,855 | 0 | 100 |

*Peak area is the integrated area under the peak and is proportional to compound concentration.

TABLE II-continued

| Ingredients | A | B | C | D |
|---|---|---|---|---|
| B-cyclodextrin | — | 2.0 | — | 2.0 |
| PLURONIC ® | — | — | 1.50 | 1.50 |

To determine the efficacy of the β-CD in reducing the sulfur containing impurities present in the papain enzyme and its effect on dentifrice flavor, Compositions A-D were aged at ambient temperature for 8 weeks prior to quantitative HS-GC/FPD analysis. The analysis used 3.0 g of toothpaste that was equilibrated at 40° C. for 4 days. Approximately 25 milliliters of headspace gas was drawn from the sample and analyzed. The results from the analysis of the toothpastes are shown in Table III below.

TABLE III

Reduction in sulfur compounds in enzyme-containing dentifrices as measured by headspace.

| Dentifrice | Peak* 1($H_2S$) (ppb) | Peak 2 (DMS) (ppb) | Total Sulfur Conc. (ppb) | % Reduction |
|---|---|---|---|---|
| A | 174 | 110 | 285 | — |
| B | 148 | 0 | 148 | 48.1 |
| C | 150 | 207 | 357 | — |
| D | 122 | 0 | 122 | 62.8 |

*Peak measured on the chromatograph as a function of elution/retention time. Individual compounds exhibit unique elution/retention times from the chromatograph column.

The results recorded in Table III show a significant reduction in sulfur containing impurities for the papain containing toothpaste compositions in which β-CD was present (Compositions B,D) when compared to similar compositions (A, C) in which β-CD was absent. The removal of the impurity species in toothpaste compositions B and D translates into an improvement in overall product taste attributes during use of the toothpaste by consumers.

EXAMPLE III

Compositions B and D of Example II were qualitatively assessed by trained Flavorists for impurity imparted meaty/broth type notes derived from the presence of papain in the compositions. The organoleptic findings of the Flavorist recorded in Table IV below demonstrate a significant improvement in product taste attributes, most notably a significant reduction in the meaty notes introduced by sulfur based impurities in papain relative to comparative Compositions A,C in which β-CD was not present:

TABLE IV

Flavorist evaluation of enzyme-containing dentifrices with and without β-CD

| Dentifrice | Reduction in Meaty/Broth-type Notes |
|---|---|
| A | — |
| B | Yes (vs. Dentifrice A) |
| C | — |
| D | Yes (vs. Dentifrice C) |

The results recorded in Table IV confirm the improvement in organoleptic qualities brought about by a significant reduction in sulfur-based impurities introduced by the papain enzyme utilizing the β-CD complex with the attendant advantage that a lesser flavor concentration is needed to mask the negative taste attributes of the impurities.

We claim:

1. An antiplaque oral care composition comprising:
   an enzyme comprising an impurity;
   and a cyclodextrin
   wherein the cyclodextrin forms a complex with the impurity,
   wherein the complex formed between the cyclodextrin and the impurity is insoluble in the antiplaque oral care composition.
2. The composition of claim 1, wherein the enzyme is a proteolytic enzyme.
3. The composition of claim 1, wherein the enzyme is papain.
4. The composition of claim 1, wherein the enzyme is present in an amount of about 0.1 to about 5% by weight.
5. The composition of claim 1, wherein the cyclodextrin is .beta. cyclodextrin.
6. The composition of claim 1, wherein the cyclodextrin is present in an amount of about 0.1 to about 5% by weight.
7. The composition of claim 1, wherein the weight ratio of the cyclodextrin to the enzyme is about 4 to about 1.
8. The composition of claim 1 wherein the impurity is water insoluble.
9. The composition of claim 1 wherein the impurity is lipophylic.
10. The composition of claim 1 wherein the impurity is a volatile sulfur compound.
11. The composition of claim 1 wherein the impurity is a ketone.
12. The composition of claim 1 wherein the impurity is selected form the group consisting of carbonyl sulfide, acetone, methyl ethyl ketone, dimethyl sulfide, carbon disulfide, mesityl oxide, hydrogen sulfide, and combinations thereof.
13. The composition of claim 1 which is a dentifrice.
14. The composition of claim 1 which is a toothpaste.
15. The composition of claim 1 which is a mouthwash.

* * * * *